(12) United States Patent
Garritano et al.

(10) Patent No.: US 7,096,728 B2
(45) Date of Patent: Aug. 29, 2006

(54) POLYMER MELT AND ELASTOMER EXTENSION FIXTURE

(75) Inventors: Ron Garritano, Monroe Township, NJ (US); John Berting, Wilmington, DE (US)

(73) Assignee: Waters Investment, LTD, New Castle, DE (US)

( * ) Notice: Subject to any disclaimer, the term of this patent is extended or adjusted under 35 U.S.C. 154(b) by 117 days.

(21) Appl. No.: 10/911,553

(22) Filed: Aug. 5, 2004

(65) Prior Publication Data

US 2005/0252280 A1 Nov. 17, 2005

Related U.S. Application Data

(60) Provisional application No. 60/570,476, filed on May 13, 2004.

(51) Int. Cl.
*G01L 5/04* (2006.01)
*G01N 3/08* (2006.01)

(52) U.S. Cl. .............................. 73/160; 73/826; 73/829

(58) Field of Classification Search ................. 73/160, 73/826, 833, 831, 832, 841, 843, 846, 847
See application file for complete search history.

(56) References Cited

U.S. PATENT DOCUMENTS 2,666,324 A * 1/1954 Stott ........................... 73/847
3,664,182 A * 5/1972 Butler ......................... 73/794
6,578,413 B1 6/2003 Sentmanat
6,691,569 B1 * 2/2004 Sentmanat ................... 73/261

OTHER PUBLICATIONS

Barnes et al. "Controlled-Stress Rotational Rheometry: An Historical Review", Korea-Australia Rheology Jornal, vol. 15, No. 4, pp. 187-196 (2003).
Meissner, J. "Development of a Universal Extensional Rhoemeter for the Uniaxial Extension of Polymer Melts" Transactions of the Society of Rheology, vol. 16:3 pp. 405-420 (1972).
Meissner et al. "A New Elongational Rheometer for Polymer Melts and Other Highly Viscoelastic Liquids" Rheological Acta 33:1-21 (1994).
Padmanabhan et al. "Transient Extensional Viscosity from a Rotational Shear Rheometer Using Fiber-Windup Technique", Journal Rheology 40, pp. 473-481 (1996).

* cited by examiner

*Primary Examiner*—Michael Cygan
(74) *Attorney, Agent, or Firm*—Pillsbury Winthrop Shaw Pittman LLP

(57) ABSTRACT

A system for making extensional measurements on a sample includes an armature, a motor drive shaft, a moveable cylinder, and a fixed cylinder. The motor drive shaft is attached to the armature. The moveable cylinder is mounted on the armature. The sample is stretched between the moveable cylinder and fixed cylinder by the rotation of the moveable cylinder around the axis of the fixed cylinder and rotation of the moveable cylinder about its own axis. The resistance of the sample produces a torque on the moveable cylinder and the fixed cylinder. The torque is measured on the moveable cylinder or on a transducer shaft attached to the fixed cylinder. The system is adaptable to a commercial rotational rheometer.

30 Claims, 9 Drawing Sheets

POLYMER MELT AND ELASTOMER EXTENSION FIXTURE

CROSS-REFERENCE TO RELATED APPLICATION

This application claims the benefit of U.S. Provisional Patent Application Ser. No. 60/570,476 filed May 13, 2004, which is herein incorporated by reference in its entirety.

BACKGROUND OF THE INVENTION

1. Field of the Invention

Embodiments of the present invention relate to systems and methods for polymer melt characterization and elastomer testing using a rheometer. More particularly, embodiments of the present invention relate to systems and methods for measuring the extensional properties of a polymer melt or elastomer sample on a rotational rheometer.

2. Background Information

Extensional measurement instruments are used to measure the viscosity and stress relaxation of samples including polymers, elastomers, and rubber compounds. These instruments are also useful in optimizing the throughput of material processing operations. These operations include fiber spinning, film blowing, blow molding, and sheet casting. Extensional measurement instruments are referred to as extensional rheometers. U.S. Pat. No. 6,578,413 to Sentmanat (the '413 patent) describes different extensional rheometers that have been developed in the prior art.

Dedicated extensional rheometers, however, are cost prohibitive, difficult to use, and have limited utility. As a result, fixtures have been developed that allow extensional measurements to be made using commercial rotational rheometers. The '413 patent describes an extensional rheometer fixture. This fixture includes a drive shaft connected to an armature. The armature is further connected to a torque shaft, and two rotatable drums are mounted in the armature. One end of a sample is connected to each drum. Both drums are rotated, stretching the sample. The torque in the fixture caused by the stretching of the sample is measured.

One problem with the fixture described in the '413 patent is the effect that the friction in the bearings of both drums and the friction in the gearing mechanism of both drums have on the measurement of torque. Because of this friction, the torque cannot be measured directly. Instead, the torque on the sample must be calculated from the measured torque and the effects of the friction.

In view of the foregoing, it can be appreciated that a substantial need exists for systems and methods that can advantageously allow extensional measurements to be made more directly using commercial rotational rheometers.

BRIEF SUMMARY OF THE INVENTION

A preferred embodiment of the present invention is a system for measuring the extensional properties of a sample that includes an armature, a motor drive shaft, a transducer shaft, a moveable cylinder, and a fixed cylinder. The motor drive shaft is attached to the armature. The moveable cylinder is mounted on the armature. The fixed cylinder is attached to the transducer shaft. The moveable cylinder and the fixed cylinder are substantially equal in size. The moveable cylinder and the fixed cylinder are in proximity to one another. The sample is attached to the moveable cylinder and the fixed cylinder so that the portion of the sample not touching the moveable cylinder and not touching the fixed cylinder extends from a tangent of the moveable cylinder to a tangent of the fixed cylinder. The moveable cylinder is rotated around an axis of the fixed cylinder by rotating the motor drive shaft at a substantially constant rotation speed. The moveable cylinder is also rotated about its own axis at substantially the same substantially constant rotation speed. A resistance from the sample is created as the sample is stretched between the moveable cylinder and the fixed cylinder by the rotation of the moveable cylinder around the axis of the fixed cylinder and the rotation of the moveable cylinder about its own axis. A torque on the fixed cylinder is created by the resistance from the sample and is translated to the transducer shaft. This torque on the transducer shaft is measured. This embodiment is particularly advantageous in that it allows the torque from the sample to be read without needing to account for the effects of friction in the gearing mechanism or the bearings.

This embodiment is adapted to a separate motor and transducer rheometer. The motor drive shaft is driven by the motor of the separate motor and transducer rheometer. The transducer shaft is the transducer shaft of the separate motor and transducer rheometer. The torque on the transducer shaft is read directly by the separate motor and transducer rheometer.

Another embodiment of the present invention is a system for measuring the extensional properties of a sample that includes an armature, a motor drive shaft, a moveable cylinder, and a fixed cylinder. The motor drive shaft is attached to the armature. The moveable cylinder is mounted on the armature. The moveable cylinder and the fixed cylinder are substantially equal in size. The moveable cylinder and the fixed cylinder are in proximity to one another. The sample is attached to the moveable cylinder and the fixed cylinder so that the portion of the sample not touching the moveable cylinder and not touching the fixed cylinder extends from a tangent of the moveable cylinder to a tangent of the fixed cylinder. The moveable cylinder is rotated around an axis of the fixed cylinder by rotating the motor drive shaft at a substantially constant rotation speed. The moveable cylinder is also rotated about its own axis at substantially the same substantially constant rotation speed. A resistance from the sample is created as the sample is stretched between the moveable cylinder and the fixed cylinder by the rotation of the moveable cylinder around the axis of the fixed cylinder and the rotation of the moveable cylinder about its own axis. A torque on the moveable cylinder is created by the resistance from the sample. This torque is measured on the moveable cylinder.

This embodiment is adapted to a combined motor and transducer rheometer. The motor drive shaft is driven by the motor of the combined motor and transducer rheometer. The fixed cylinder is mounted to a frame of the combined motor and transducer rheometer. The torque created by the resistance from the sample is translated through a gearing mechanism to the motor drive shaft. The torque on the motor drive shaft due to the resistance from the sample is determined by the combined motor and transducer rheometer.

Figure 1:
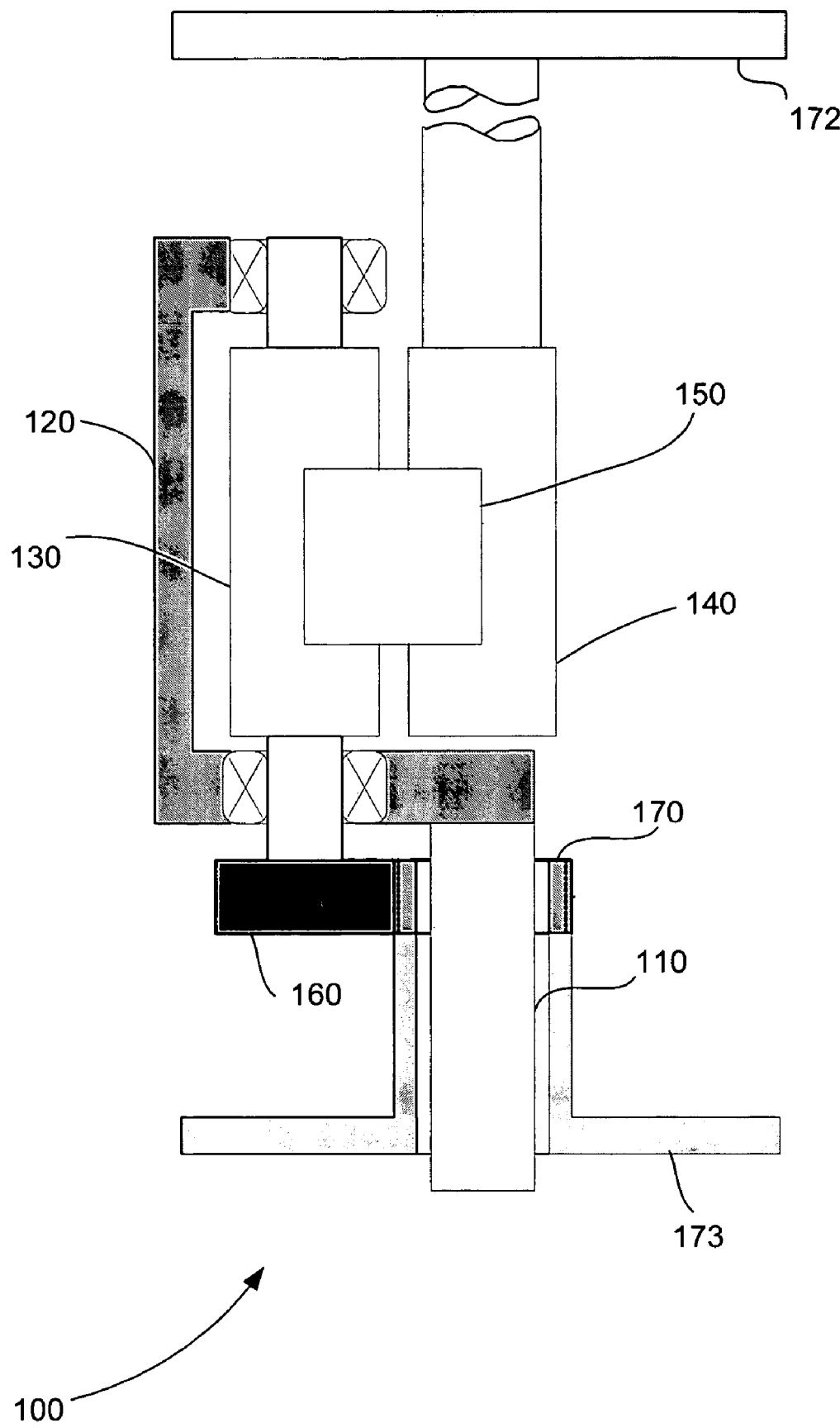
FIG. 1 is a schematic diagram showing a system for measuring the extensional properties of a sample that includes an armature, a motor drive shaft, a moveable cylinder, and a fixed cylinder, in accordance with an embodiment of the present invention.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

FIG. 1 is a schematic diagram showing a system for measuring the extensional properties of a sample that includes an armature, a motor drive shaft, a moveable cylinder, and a fixed cylinder, in accordance with an embodiment of the present invention. In system 100, motor drive shaft 110 is attached to armature 120. Moveable cylinder 130 is mounted on armature 120. Fixed cylinder 140 is fixed, for example, to a frame or housing 172. Fixed cylinder 140 is located in close proximity to moveable cylinder 130. Decreasing the distance between fixed cylinder 140 and moveable cylinder 130 increases the amount of strain on sample 150 that can be produced per rotation of moveable cylinder 130 about the axis of fixed cylinder 140 and about its own axis. The minimum distance possible between fixed cylinder 140 and moveable cylinder 130 is approximately twice the thickness of sample 150 due to the build up of sample 150 on the two cylinders. An exemplary sample thickness is about one millimeter. A minimum distance between fixed cylinder 140 and moveable cylinder 130 for this exemplary sample is, therefore, about two millimeters. The maximum distance between fixed cylinder 140 and moveable cylinder 130 is limited only by the dimensions of the oven into which the invention is placed.

In a preferred embodiment of the system, moveable cylinder 130 and fixed cylinder 140 are aligned in parallel.

Moveable cylinder 130 and fixed cylinder 140 are substantially equal in size. In a preferred embodiment of the system, the radius of moveable cylinder 130 is substantially equivalent to the radius of fixed cylinder 140. In another embodiment of the system, the height of moveable cylinder 130 is substantially equivalent to the height of fixed cylinder 140. The height of the cylinders is typically about twenty millimeters and the radius of each of the cylinders is typically about five millimeters.

Sample 150 is attached to moveable cylinder 130 and fixed cylinder 140 so that the portion of sample 150 not touching moveable cylinder 130 and fixed cylinder 140 extends from a tangent of moveable cylinder 130 to a tangent of the fixed cylinder 140. The initial length of sample 150 is, therefore, greater than or equal to the sum of the radius of moveable cylinder 130 and the radius of fixed cylinder 140. In a preferred embodiment of the system, the initial length of sample 150 that is attached between moveable cylinder 130 and fixed cylinder 140 is substantially orthogonal to both the axis of moveable cylinder 130 and the axis of fixed cylinder 140.

Sample 150 is stretched between moveable cylinder 130 and fixed cylinder 140 by the rotation of moveable cylinder 130 in two different ways. First, moveable cylinder 130 and armature 120 are rotated around fixed cylinder 140 by rotating motor drive shaft 110 at a substantially constant rotation speed. Second, moveable cylinder 130 is rotated about its own axis at substantially the same substantially constant rotation speed. In a preferred embodiment of system 100, moveable gearing mechanism 160 is connected to fixed gearing mechanism 170. Fixed gearing mechanism 170 is fixed to, for example, a frame or motor housing 173, which could be the same as or different from housing 172. As motor drive shaft 110 is turned, moveable gearing mechanism 160 moves around fixed gearing mechanism 170 causing moveable cylinder 130 to rotate about its own axis. Fixed gearing mechanism 170 is not connected to motor drive shaft 110. Motor drive shaft 110 rotates moveable cylinder 130 about its own axis at substantially the same time as motor drive shaft 110 rotates moveable cylinder 130 and armature 120 around the axis of fixed cylinder 140.

In one embodiment of the present invention, moveable cylinder 130 rotates about its own axis in substantially the same angular direction as moveable cylinder 130 rotates around the axis of fixed cylinder 140. In another embodiment, moveable cylinder 130 rotates about its own axis in substantially the opposite angular direction as moveable cylinder 130 rotates around the axis of fixed cylinder 140.

In a preferred embodiment of system 100, the length of the portion of sample 150 that is not touching moveable cylinder 130 and fixed cylinder 140 is held substantially constant during the rotation of moveable cylinder 130 and armature 120 around the axis of fixed cylinder 140 and the rotation of moveable cylinder 130 about its own axis. This length is also the portion of sample 150 that is stretched. This "free" length, or stretched length, of sample 150 is supported by moveable cylinder 130 and fixed cylinder 140 at ends tangent to moveable cylinder 130 and tangent to fixed cylinder 140. In a preferred embodiment of system 100, the length of sample 150 taken up by the circumference of moveable cylinder 130 and the length of sample 150 taken up by the circumference of fixed cylinder 140 are substantially equivalent during the rotation of moveable cylinder 130 and armature 120 around the axis of fixed cylinder 140 and the rotation of moveable cylinder 130 about its own axis.

The force opposing the stretching of sample 150 between moveable cylinder 130 and fixed cylinder 140 is the resistance from sample 150. This resistance produces a torque on moveable cylinder 130, which is measured on moveable cylinder 130. In a preferred embodiment of system 100, this torque is translated through gearing mechanism 160 to motor drive shaft 110 and is measured on motor drive shaft 110.

In another embodiment of the present invention, system 100 is a fixture for a combined motor and transducer (CMT) rheometer (not shown). Motor drive shaft 110 is driven by the motor of the CMT rheometer. Fixed cylinder 140 is mounted to the frame of the CMT rheometer. The torque due to the resistance from sample 150 is translated through gearing mechanism 160 to motor drive shaft 110. This torque is determined by subtracting the torque due to the motor drive mechanism of the CMT rheometer from the total torque measured on motor drive shaft 110. The total torque on motor drive shaft 110 is determined from a motor current of the CMT rheometer.

Figure 2:
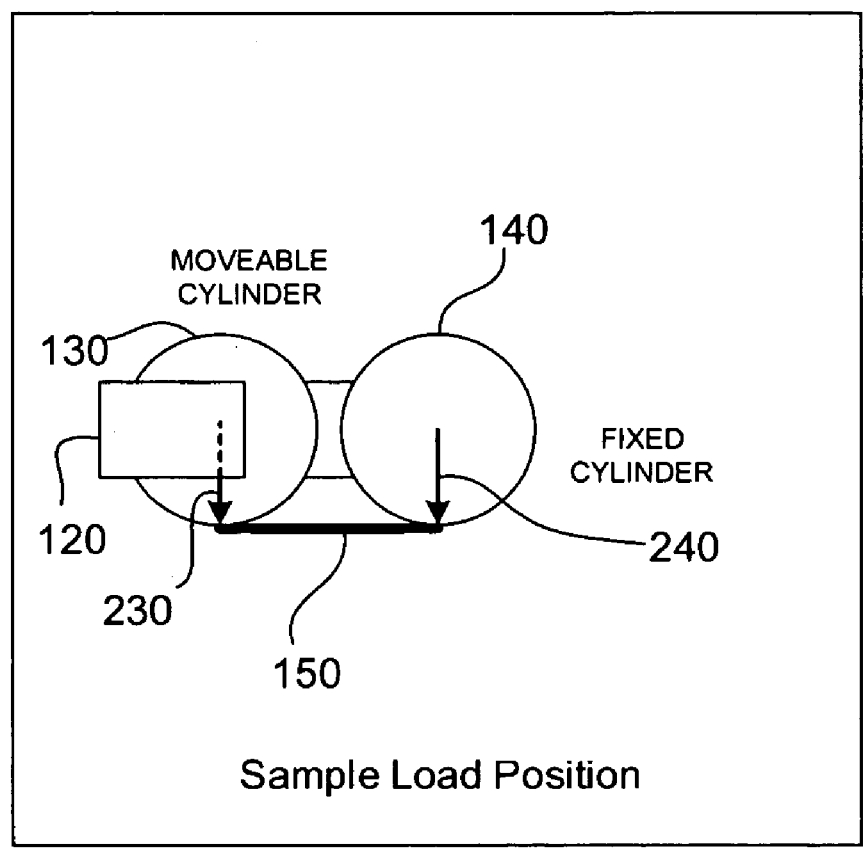
FIG. 2 is a schematic diagram of an axial view of the sample load position of the armature, the moveable cylinder, the fixed cylinder, and the sample of a system for measuring the extensional properties of the sample, in accordance with an embodiment of the present invention.

The movement of armature 120, moveable cylinder 130, and sample 150 about fixed cylinder 140 in system 100 is illustrated in FIGS. 2–5. FIG. 2 is an axial view 200 of the sample load position of armature 120, moveable cylinder 130, fixed cylinder 140, and sample 150, before moveable cylinder 130 starts moving, in accordance with an embodiment of the present invention. In view 200, sample 150 is shown attached from the tangent of moveable cylinder 130 to the tangent of fixed cylinder 140. The initial length of sample 150 is, therefore, equal to or greater than the sum of the radius of moveable cylinder 130 and the radius of fixed cylinder 140. The radius of moveable cylinder 130 and the radius of fixed cylinder 140 preferably are substantially equivalent. In view 200, moveable cylinder 130 and armature 120 have not yet been rotated and are, therefore, shown at an angle of zero degrees with respect to fixed cylinder 140. Arrow 230 shows the position of moveable cylinder 130 with respect to its axis and armature 120. Arrow 240 shows the position of fixed cylinder 140 with respect to its axis.

Figure 3:
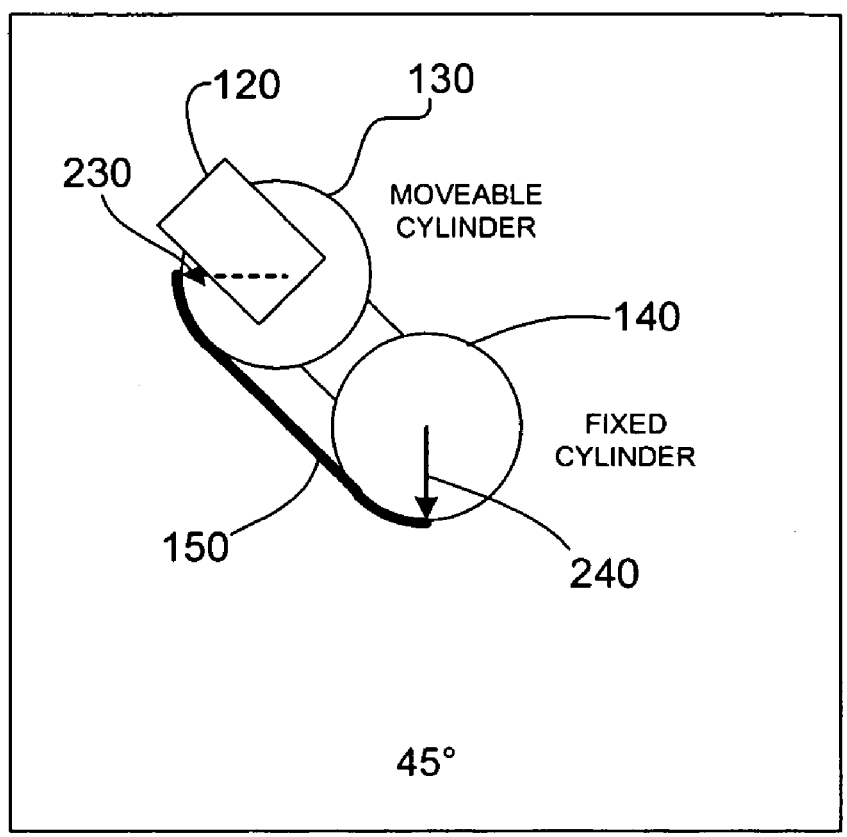
FIG. 3 is a schematic diagram of an axial view of the position of the armature, the moveable cylinder, the fixed cylinder, and the sample of a system for measuring the extensional properties of the sample after the moveable cylinder has rotated forty-five degrees around the axis of the fixed cylinder and forty-five degrees about its own axis, in accordance with an embodiment of the present invention.
Figure 3:
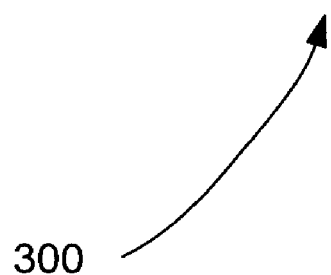

FIG. 3 is an axial view 300 of the position of armature 120, moveable cylinder 130, fixed cylinder 140, and sample 150 after moveable cylinder 130 has rotated forty-five degrees around the axis of fixed cylinder 140 and forty-five degrees about its own axis, in accordance with an embodiment of the present invention. In view 300, moveable cylinder 130 and armature 120 have been rotated forty-five degrees at a substantially constant rotation speed around the axis of fixed cylinder 140 in order to stretch sample 150 between moveable cylinder 130 and fixed cylinder 140. At the same time, moveable cylinder 130 has been rotated forty-five degrees about its own axis at substantially the same substantially constant rotation speed also to stretch sample 150 between moveable cylinder 130 and fixed cylinder 140. As a result, the amount of sample 150 taken up on the circumference of moveable cylinder 130 and the amount of sample 150 taken up on the circumference of fixed cylinder 140 is substantially equivalent.

The length of sample 150 not touching either moveable cylinder 130 or fixed cylinder 140 in view 300 of FIG. 3 is substantially equivalent to the length of sample 150 not touching either moveable cylinder 130 or fixed cylinder 140 in view 200 of FIG. 2. This is the length of sample 150 providing a resistance. Arrow 240 in view 200 of FIG. 2 and arrow 240 in view 300 of FIG. 3 are in the same location, showing that fixed cylinder 140 has not moved about its axis from view 200 to view 300. Arrow 230, on the other hand, has rotated forty-five degrees about the axis of moveable cylinder 130 from view 200 of FIG. 2 to view 300 of FIG. 3, showing that moveable cylinder 130 has rotated forty-five degrees about its own axis from view 200 to view 300.

Figure 4:
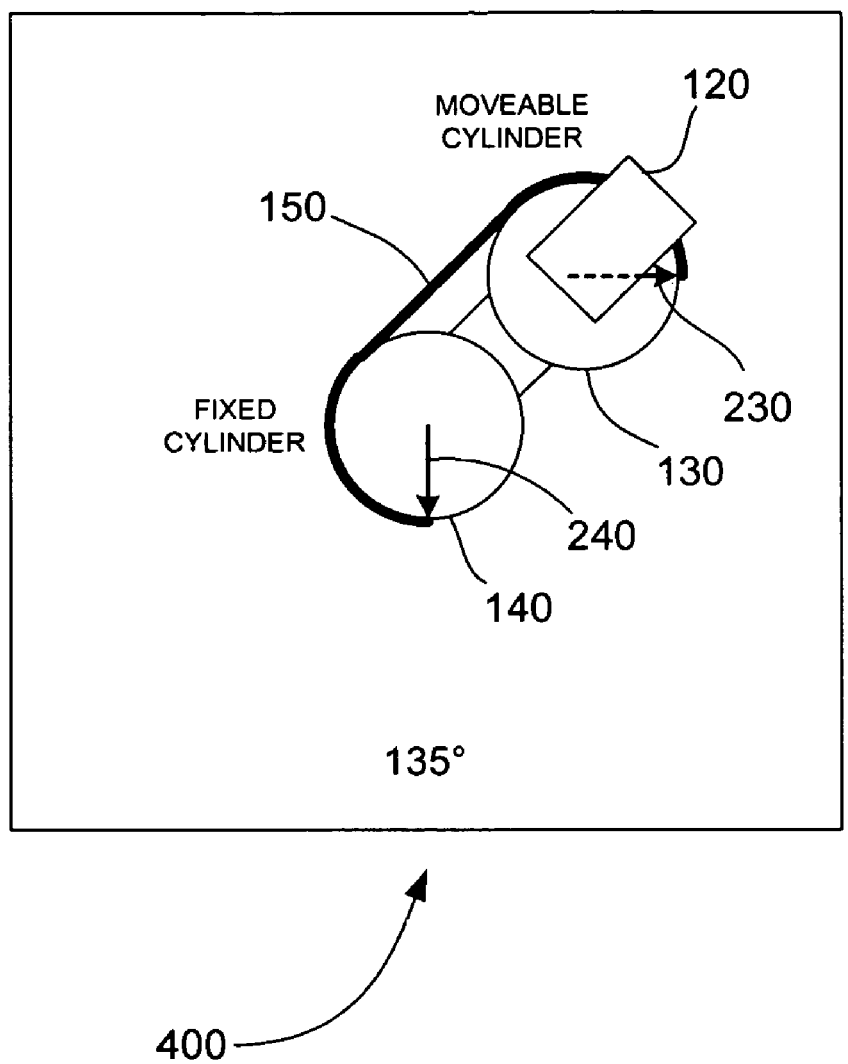
FIG. 4 is a schematic diagram of an axial view the position of the armature, the moveable cylinder, the fixed cylinder, and the sample of a system for measuring the extensional properties of the sample after the moveable cylinder has been rotated one hundred thirty-five degrees around the axis of the fixed cylinder and one hundred thirty-five degrees about its own axis, in accordance with an embodiment of the present invention.

FIG. 4 is an axial view 400 of the position of armature 120, moveable cylinder 130, fixed cylinder 140, and sample 150 after moveable cylinder 130 has rotated one hundred thirty-five degrees around the axis of fixed cylinder 140 and one hundred thirty-five degrees about its own axis, in accordance with an embodiment of the present invention. In view 400, more of sample 150 has been taken up on the circumference of moveable cylinder 130 and the circumference of fixed cylinder 140 than in view 300 of FIG. 3, while the length of sample 150 not touching moveable cylinder 130 or fixed cylinder 140 has remained the same as it was in view 300. Arrow 240 shows that fixed cylinder 140 has not rotated about its axis. Arrow 230, however, shows that moveable cylinder 130 has rotated one hundred thirty-five degrees about its own axis from view 200 of FIG. 2 to view 400 of FIG. 4.

Figure 5:
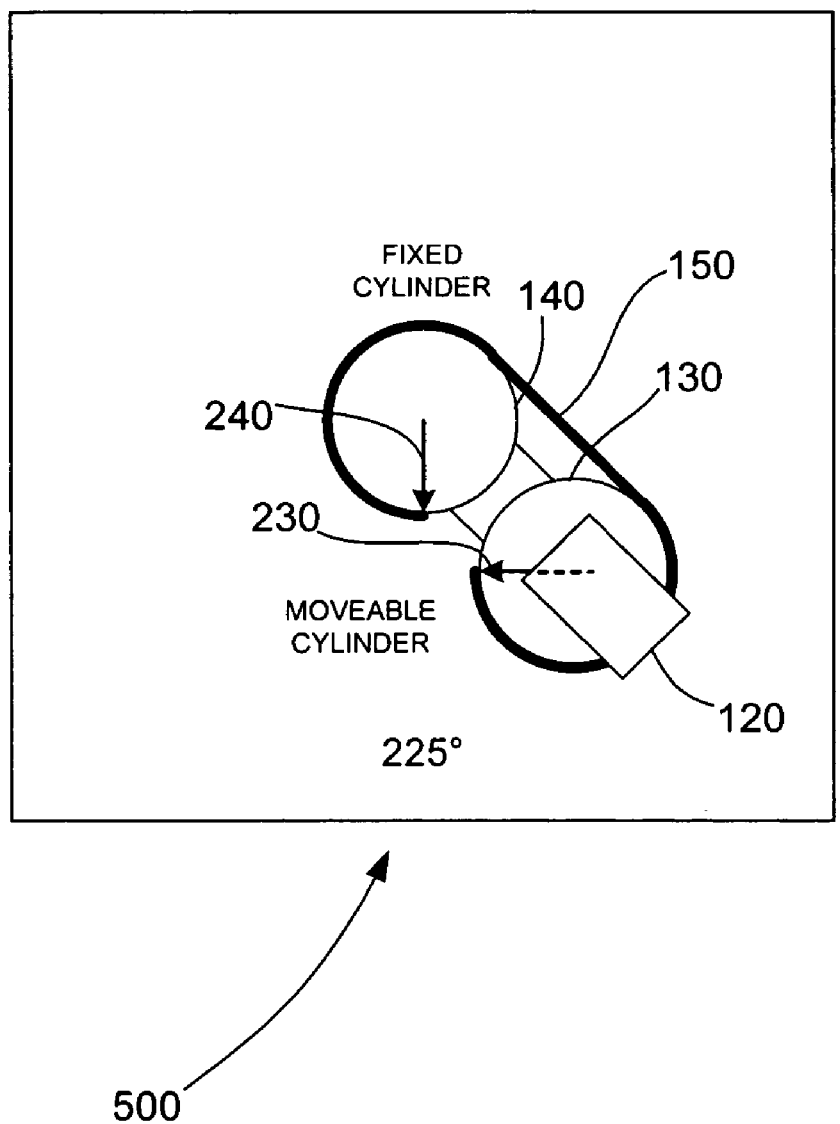
FIG. 5 is a schematic diagram of an axial view of the position of the armature, the moveable cylinder, the fixed cylinder, and the sample of a system for measuring the extensional properties of the sample after the moveable cylinder has rotated two hundred twenty-five degrees around the axis of the fixed cylinder and two hundred twenty-five degrees about its own axis, in accordance with an embodiment of the present invention.

FIG. 5 is an axial view 500 of the position of armature 120, moveable cylinder 130, fixed cylinder 140, and sample 150 after moveable cylinder 130 has rotated two hundred twenty-five degrees around the axis of fixed cylinder 140 and two hundred twenty-five degrees about its own axis, in accordance with an embodiment of the present invention. In view 500, even more of sample 150 has been taken up on the circumference of moveable cylinder 130 and the circumference of fixed cylinder 140 than in view 400 of FIG. 4. Also, the length of sample 150 not touching moveable cylinder 130 or fixed cylinder 140 has remained the same as it was in view 400 of FIG. 4. Arrow 240 shows that fixed cylinder 140 has not rotated about its axis. Arrow 230, however, shows that moveable cylinder 130 has rotated two hundred twenty-five degrees about its axis from view 200 of FIG. 2 to view 500 of FIG. 5.

As shown in FIGS. 3–5, the amount of sample 150 taken up on the circumference of moveable cylinder 130 and fixed cylinder 140 increases as moveable cylinder 130 and armature 120 rotate around the axis of fixed cylinder 140 and as moveable cylinder 130 rotates on its own axis. Referring again the side view shown in FIG. 1, if the length of sample 150 attached between moveable cylinder 130 and fixed cylinder 140 is orthogonal to the axis of moveable cylinder 130 and the axis of fixed cylinder 140, then the circumference of moveable cylinder 130 and the circumference of fixed cylinder 140 will be completely covered with sample 150 after moveable cylinder 130 makes one complete rotation around the axis of fixed cylinder 140 and moveable cylinder 130 makes one complete rotation about its own axis.

Figure 6:
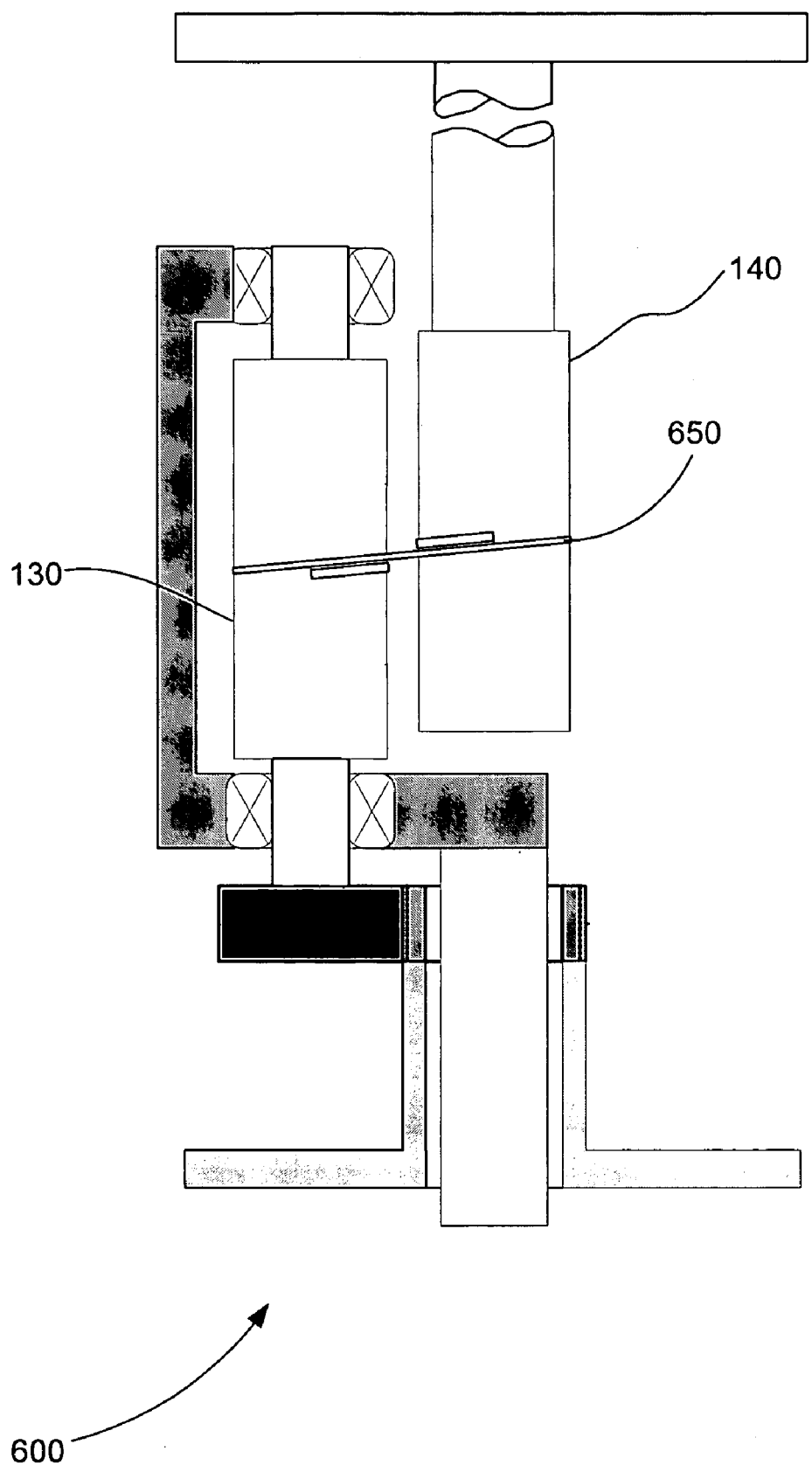
FIG. 6 is a schematic diagram showing a system for measuring the extensional properties of a sample that includes an armature, a motor drive shaft, a moveable cylinder, and a fixed cylinder, where the moveable cylinder and the fixed cylinder are axially separated near the end of travel, in accordance with an embodiment of the present invention.
Figure 7:
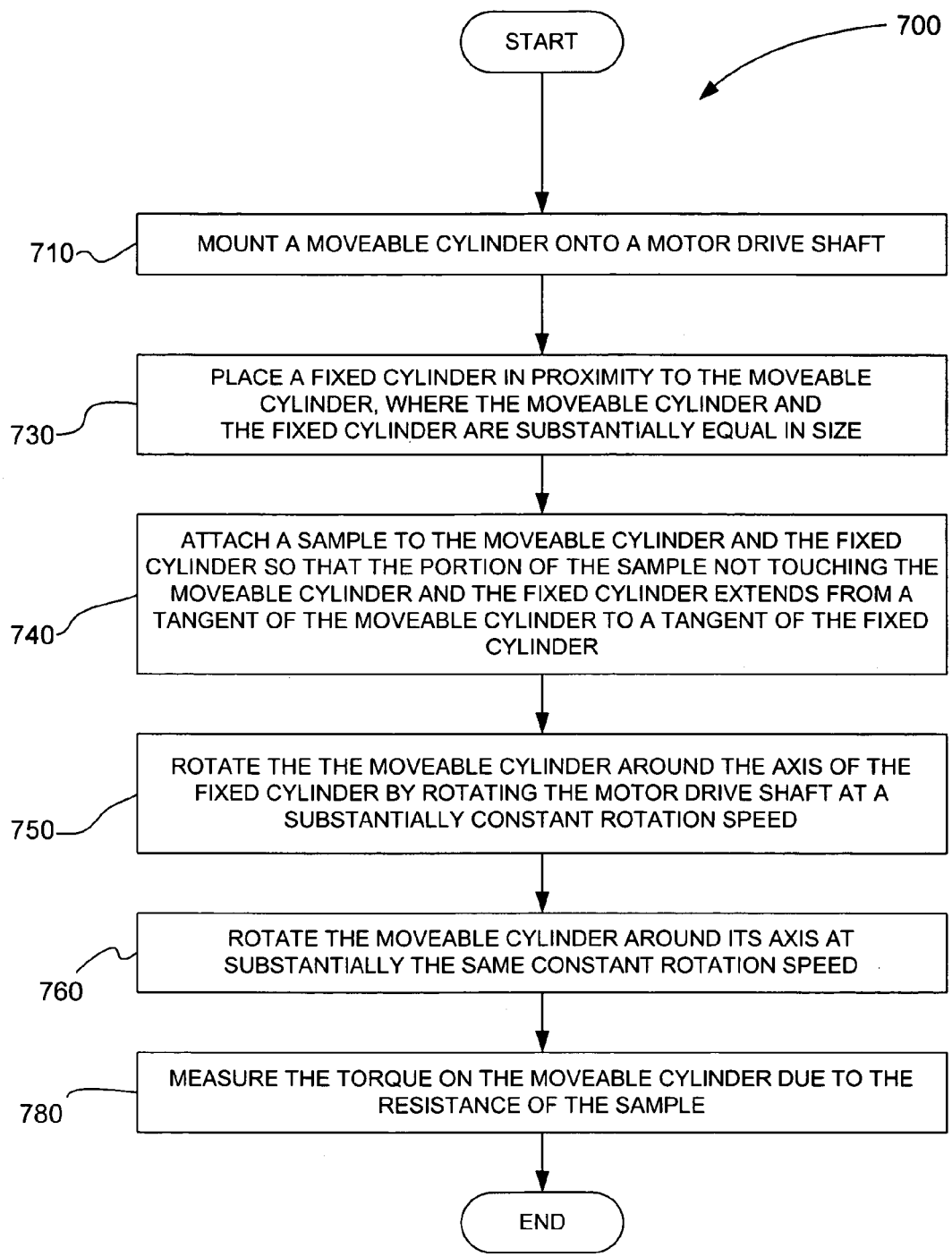
FIG. 7 is a flowchart showing a method for measuring the extensional properties of a sample using a system that includes a motor drive shaft, a moveable cylinder, and a fixed cylinder, in accordance with an embodiment of the present invention.

FIG. 6 is a schematic diagram showing a system 600 for measuring the extensional properties of a sample that includes an armature, a motor drive shaft, a moveable cylinder, and a fixed cylinder, where the moveable cylinder and the fixed cylinder are axially separated near the end of travel, in accordance with an embodiment of the present invention. In system 600, a mechanism is provided to increase the axial separation of moveable cylinder 130 and fixed cylinder 140 during the rotation of moveable cylinder 130 around the axis of fixed cylinder 140 and about its own axis. The length of sample 650 stretched between moveable cylinder 130 and fixed cylinder 140 is not substantially orthogonal to the axis of moveable cylinder 130 and the axis of fixed cylinder 140. This allows sample 650 to be taken up in a helical rather than a circular pattern on the circumference of moveable cylinder 130 and the circumference of fixed cylinder 140. This helical pattern provides additional space for used sample on both cylinders and allows moveable cylinder 130 to make more than one complete rotation around the axis of fixed cylinder 140 and about its own axis. This increase in axial separation allows the length of sample 650 that is stretched between moveable cylinder 130 and fixed cylinder 140 to remain substantially constant as moveable cylinder 130 is rotated around the axis of fixed cylinder 140 and about its own axis. The axial separation of moveable cylinder 130 and fixed cylinder 140 is accomplished by moving moveable cylinder 130 along its axis, moving fixed cylinder 140 along its axis, or moving both moveable cylinder 130 along its axis and fixed cylinder 140 along its axis FIG. 7 is a flowchart showing a method 700 for measuring the extensional properties of a sample using a system that includes a motor drive shaft, a moveable cylinder, and a fixed cylinder, in accordance with an embodiment of the present invention.

In step 710 of method 700, a moveable cylinder is mounted on a motor drive shaft. Preferably, the moveable cylinder is mounted on the motor drive shaft using an armature.

In step 730, a fixed cylinder is placed in proximity to the moveable cylinder. The fixed cylinder and the moveable cylinder are substantially equal in size.

In step 740, a sample is attached to the moveable cylinder and the fixed cylinder so that the portion of the sample that does not touch either the moveable cylinder or the fixed cylinder extends from a tangent of the moveable cylinder to a tangent of the fixed cylinder.

In step 750, the moveable cylinder is rotated around an axis of the fixed cylinder by rotating the motor drive shaft at a substantially constant rotation speed.

In step 760, the moveable cylinder is rotated about its own axis at substantially the same substantially constant rotation speed.

In response to the rotation of the moveable cylinder around the axis of the fixed cylinder and about its own axis. The sample provides a resistance as it is stretched between the moveable cylinder and the fixed cylinder.

In step 780, a torque on the moveable cylinder is measured. This torque is created by the resistance from the sample.

Figure 8:
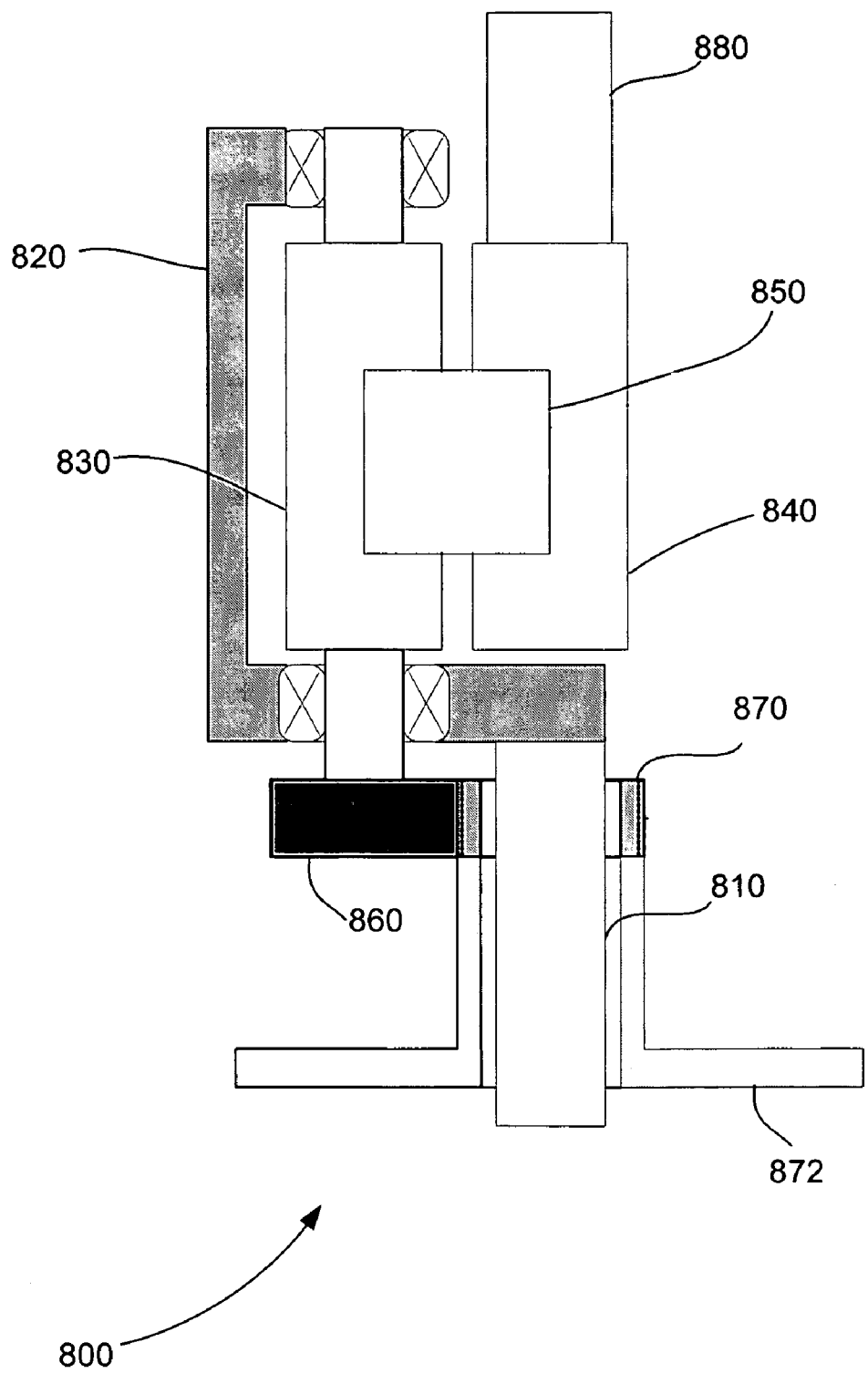
FIG. 8 is a schematic diagram showing a system for measuring the extensional properties of a sample that includes an armature, a motor drive shaft, a transducer shaft, a moveable cylinder, and a fixed cylinder, in accordance with an embodiment of the present invention.

FIG. 8 is a schematic diagram showing a system 800 for measuring the extensional properties of a sample that includes an armature, a motor drive shaft, a transducer shaft, a moveable cylinder, and a fixed cylinder, in accordance with an embodiment of the present invention. In system 800, motor drive shaft 810 is attached to armature 820. Moveable cylinder 830 is mounted on armature 820. Fixed cylinder 840 is attached to transducer shaft 880. Fixed cylinder 840 is located in close proximity to moveable cylinder 830. Decreasing the distance between fixed cylinder 840 and moveable cylinder 830 increases the amount of strain on sample 850 that can be produced per rotation of moveable cylinder 830 about the axis of fixed cylinder 840 and about its own axis. The minimum distance possible between fixed cylinder 840 and moveable cylinder 830 is approximately twice the thickness of sample 850 due to the build up of sample 850 on the two cylinders. An exemplary sample thickness is about one millimeter. A minimum distance between fixed cylinder 840 and moveable cylinder 830 for this exemplary sample is, therefore, about two millimeters. The maximum distance between fixed cylinder 840 and moveable cylinder 830 is limited only by the dimensions of the oven into which the invention is placed. In a preferred embodiment of the system, moveable cylinder 830 and fixed cylinder 840 are aligned in parallel.

Moveable cylinder 830 and fixed cylinder 840 are substantially equal in size. In a preferred embodiment of the system, the radius of moveable cylinder 830 is substantially equivalent to the radius of fixed cylinder 840. In another embodiment of the system, the height of moveable cylinder 830 is substantially equivalent to the height of fixed cylinder 840. The height of the cylinders is typically about twenty millimeters and the radius of each of the cylinders is typically about five millimeters.

Sample 850 is attached to moveable cylinder 830 and fixed cylinder 840 so that the portion of sample 850 not touching moveable cylinder 830 and fixed cylinder 840 extends from a tangent of moveable cylinder 830 to a tangent of the fixed cylinder 840. The initial length of sample 850 is, therefore, greater than or equal to the sum of the radius of moveable cylinder 830 and the radius of fixed cylinder 840. In a preferred embodiment of the system, the initial length of sample 850 that is attached between moveable cylinder 830 and fixed cylinder 840 is substantially orthogonal to both the axis of moveable cylinder 830 and the axis of fixed cylinder 840.

Sample 850 is stretched between moveable cylinder 830 and fixed cylinder 840 by the rotation of moveable cylinder 830 in two different ways. First, moveable cylinder 830 and armature 820 are rotated around fixed cylinder 840 by rotating motor drive shaft 810 at a substantially constant rotation speed. Second, moveable cylinder 830 is rotated about its own axis at substantially the same substantially constant rotation speed. In a preferred embodiment of system 800, moveable gearing mechanism 860 is connected to fixed gearing mechanism 870. Fixed gearing mechanism 870 is fixed to, for example, a frame or motor housing 872. As motor drive shaft 810 is turned, moveable gearing mechanism 860 moves around fixed gearing mechanism 870 causing moveable cylinder 830 to rotate about its own axis. Fixed gearing mechanism 870 is not connected to motor drive shaft 810. Motor drive shaft 810 rotates moveable cylinder 830 about its own axis at substantially the same time as motor drive shaft 810 rotates moveable cylinder 830 and armature 820 around the axis of fixed cylinder 840.

In one embodiment of the present invention, moveable cylinder 830 rotates about its own axis in substantially the same angular direction as moveable cylinder 830 rotates around the axis of fixed cylinder 840. In another embodiment, moveable cylinder 830 rotates about its own axis in substantially the opposite angular direction as moveable cylinder 830 rotates around the axis of fixed cylinder 840.

In a preferred embodiment of system 800, the length of the portion of sample 850 that is not touching moveable cylinder 830 and fixed cylinder 840 is held substantially constant during the rotation of moveable cylinder 830 and armature 820 around the axis of fixed cylinder 840 and the rotation of moveable cylinder 830 about its own axis. This length is also the portion of sample 850 that is stretched. This "free" length, or stretched length, of sample 850 is supported by moveable cylinder 830 and fixed cylinder 840 at ends tangent to moveable cylinder 830 and tangent to fixed cylinder 840. In a preferred embodiment of system 800, the length of sample 850 taken up by the circumference of moveable cylinder 830 and the length of sample 850 taken up by the circumference of fixed cylinder 840 are substantially equivalent during the rotation of moveable cylinder 830 and armature 820 around the axis of fixed cylinder 840 and the rotation of moveable cylinder 830 about its own axis.

The force opposing the stretching of sample 850 between moveable cylinder 830 and fixed cylinder 840 is the resistance from sample 850. This resistance produces a torque on fixed cylinder 840. This torque is translated from fixed cylinder 840 to the attached transducer shaft 880 and is measured on transducer shaft 880.

In another embodiment of the present invention, system 800 is a fixture for a separate motor and transducer (SMT) rheometer (not shown). Motor drive shaft 810 is driven by the motor of the SMT rheometer. Transducer shaft 880 is the transducer shaft of the SMT rheometer.

In another embodiment of this system, a mechanism is provided to increase the axial separation, or separation along the axes of the cylinders, of moveable cylinder 830 and fixed cylinder 840 during the rotation of moveable cylinder 830 around the axis of fixed cylinder 840 and about its own axis. The length of sample 850 stretched between moveable cylinder 830 and fixed cylinder 840 is not substantially orthogonal to the axis of moveable cylinder 830 and the axis of fixed cylinder 840. This allows sample 850 to be taken up in a helical rather than a circular pattern on the circumference of moveable cylinder 830 and the circumference of fixed cylinder 840. This helical pattern provides additional space for used sample on both cylinders and allows moveable cylinder 830 to make more than one complete rotation around the axis of fixed cylinder 840 and about its own axis. This increase in axial separation allows the length of sample 850 that is stretched between moveable cylinder 830 and fixed cylinder 840 to remain substantially constant as moveable cylinder 830 is rotated around the axis of fixed cylinder 840 and about its own axis. The axial separation of moveable cylinder 830 and fixed cylinder 840 is accomplished by moving moveable cylinder 830 along its axis, moving fixed cylinder 840 along its axis, or moving both moveable cylinder 830 along its axis and fixed cylinder 840 along its axis.

Figure 9:
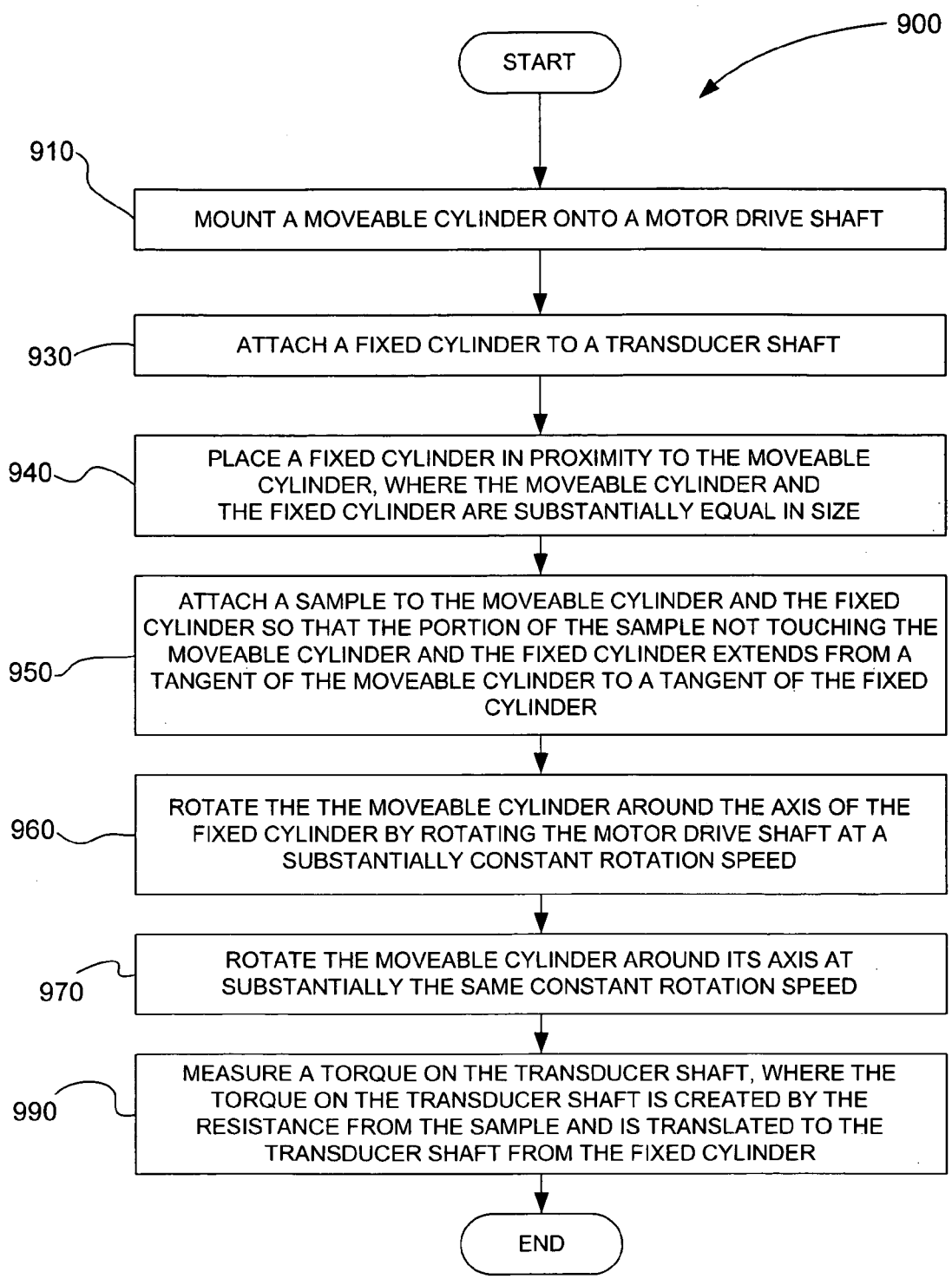
FIG. 9 is a flowchart showing a method for measuring the extensional properties of a sample using a system that includes a motor drive shaft, a transducer shaft, a moveable cylinder, and a fixed cylinder, in accordance with an embodiment of the present invention.

FIG. 9 is a flowchart showing a method 900 for measuring the extensional properties of a sample using a system that includes a motor drive shaft, a transducer shaft, a moveable cylinder, and a fixed cylinder, in accordance with an embodiment of the present invention.

In step 910 of method 900, a moveable cylinder is mounted on a motor drive shaft. Preferably, the moveable cylinder is mounted on the motor drive shaft using an armature.

In step 930, a fixed cylinder is attached to a transducer shaft.

In step 940, the fixed cylinder is placed in proximity to the moveable cylinder. The fixed cylinder and the moveable cylinder are substantially equal in size.

In step 950, a sample is attached to the moveable cylinder and the fixed cylinder so that the portion of the sample that does not touch either the moveable cylinder or the fixed cylinder extends from a tangent of the moveable cylinder to a tangent of the fixed cylinder.

In step 960, the moveable cylinder is rotated around an axis of the fixed cylinder by rotating the motor drive shaft at a substantially constant rotation speed.

In step 970, the moveable cylinder is rotated about its own axis at substantially the same substantially constant rotation speed.

In step 980, a resistance from the sample is created as the sample is stretched between the moveable cylinder and the fixed cylinder by the rotation of the moveable cylinder around the axis of the fixed cylinder and about its own axis.

In step 990, a torque on the transducer shaft is measured. The torque on the transducer shaft is created by the resistance from the sample and is translated to the transducer shaft from the fixed cylinder.

Systems and methods in accordance with embodiments of the present invention disclosed herein allow extensional measurements to be made with commercial rotational rheometers more easily and directly. The number of moving parts in these systems and methods is minimized, reducing the overall cost. In addition, the extensional measurements in these systems and methods are made closer to the sample, providing more accurate results.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for measuring the extensional properties of a sample, comprising:
   an armature;
   a motor drive shaft attached to the armature;
   a transducer shaft;
   a fixed cylinder attached to the transducer shaft; and
   a moveable cylinder, wherein the sample is attached to the moveable cylinder and the fixed cylinder so that a portion of the sample not touching the moveable cylinder and not touching the fixed cylinder extends from a tangent of the moveable cylinder to a tangent of the fixed cylinder, wherein the moveable cylinder is rotated around an axis of the fixed cylinder by rotating the motor drive shaft at a substantially constant rotation speed, wherein the moveable cylinder is rotated around an axis of the moveable cylinder at approximately the substantially constant rotation speed, wherein a resistance from the sample is created as the sample is stretched between the moveable cylinder and the fixed cylinder by the rotation of the moveable cylinder around the axis of the fixed cylinder and the rotation of the moveable cylinder around the axis of the moveable cylinder, and wherein a torque on the fixed cylinder created by the resistance is translated to the transducer shaft and measured on the transducer shaft.

2. The system of claim 1, wherein the moveable cylinder and the fixed cylinder are substantially equal in size.

3. The system of claim 1, wherein the moveable cylinder and the fixed cylinder are in proximity to one another.

4. The system of claim 1, wherein the axis of the moveable cylinder and the axis of the fixed cylinder are aligned in parallel.

5. The system of claim 1, wherein a height of the moveable cylinder and a height of the fixed cylinder are substantially equivalent.

6. The system of claim 1, wherein an initial length of the sample is at least equal to a sum of a radius of the moveable cylinder and a radius of the fixed cylinder.

7. The system of claim 1, wherein a length of the portion of the sample not touching the moveable cylinder and the fixed cylinder is held substantially constant during the rotation of the moveable cylinder around the axis of the fixed cylinder and the rotation of the moveable cylinder around the axis of the moveable cylinder.

8. The system of claim 1, wherein a length of the sample that is attached to the moveable cylinder and the fixed cylinder is substantially orthogonal to the axis of the moveable cylinder and the axis of the fixed cylinder.

9. The system of claim 1, wherein a length of the sample being taken up by a circumference of the moveable cylinder and a length of the sample being taken up by a circumference of the fixed cylinder are substantially equivalent during the rotation of the moveable cylinder around the axis of the fixed cylinder and the rotation of the moveable cylinder around the axis of the moveable cylinder.

10. The system of claim 1, further comprising a gearing mechanism connecting the motor drive shaft and the moveable cylinder that rotates the moveable cylinder around the axis of the moveable cylinder as the motor drive shaft rotates the moveable cylinder around the axis of the fixed cylinder.

11. The system of claim 1, wherein the transducer shaft comprises a transducer shaft of a separate motor and transducer rheometer.

12. The system of claim 1, wherein the motor drive shaft is driven by a motor of a separate motor and transducer rheometer.

13. The system of claim 1, wherein the moveable cylinder is rotated around the axis of the fixed cylinder in substantially the same angular direction that the moveable cylinder is rotated around an axis of the moveable cylinder.

14. The system of claim 1, wherein the moveable cylinder is rotated around the axis of the fixed cylinder in substantially the opposite angular direction that the moveable cylinder is rotated around an axis of the moveable cylinder.

15. The system of claim 1, wherein the moveable cylinder and the fixed cylinder are axially separated during the rotation of the moveable cylinder around the axis of the fixed cylinder and the rotation of the moveable cylinder around the axis of the moveable cylinder.

16. The system of claim 15, wherein the portion of the sample not touching the moveable cylinder and the fixed cylinder is not substantially orthogonal to the axis of the moveable cylinder and the axis of the fixed cylinder.

17. A method for measuring the extensional properties of a sample, comprising:
   mounting a moveable cylinder onto a motor drive shaft;
   attaching a fixed cylinder to a transducer shaft;
   placing the fixed cylinder in proximity to the moveable cylinder, wherein the moveable cylinder and the fixed cylinder are substantially equal in size;
   attaching the sample to the moveable cylinder and the fixed cylinder so that a portion of the sample not touching the moveable cylinder and not touching the fixed cylinder extends from a tangent of the moveable cylinder to a tangent of the fixed cylinder;
   rotating the moveable cylinder around an axis of the fixed cylinder by rotating the motor drive shaft at a substantially constant rotation speed;
   rotating the moveable cylinder around an axis of the moveable cylinder at the substantially constant rotation speed; and
   measuring a torque on the transducer shaft, wherein the torque is created by a resistance from the sample and translated from the fixed cylinder to the transducer shaft.

18. The method of claim 17, wherein the axis of the moveable cylinder and the axis of the fixed cylinder are aligned in parallel.

19. The method of claim 17, wherein a height of the moveable cylinder and a height of the fixed cylinder are substantially equivalent.

20. The method of claim 17, wherein an initial length of the sample is at least equal to a sum of a radius of the moveable cylinder and a radius of the fixed cylinder.

21. The method of claim 17, wherein a length of the portion of the sample not touching the moveable cylinder and the fixed cylinder is held substantially constant during the rotation of the moveable cylinder around the axis of the fixed cylinder and the rotation of the moveable cylinder around the axis of the moveable cylinder.

22. The method of claim 17, wherein a length of the sample that is attached to the moveable cylinder and the fixed cylinder is substantially orthogonal to the axis of the moveable cylinder and the axis of the fixed cylinder.

23. The method of claim 17, wherein a length of the sample being taken up by a circumference of the moveable cylinder and a length of the sample being taken up by a circumference of the fixed cylinder are substantially equivalent during the rotation of the moveable cylinder around the axis of the fixed cylinder and the rotation of the moveable cylinder around the axis of the moveable cylinder.

24. The method of claim 17, further comprising providing a gearing mechanism connecting the motor drive shaft and the moveable cylinder that rotates the moveable cylinder around the axis of the moveable cylinder as the motor drive shaft rotates the moveable cylinder around the axis of the fixed cylinder.

25. The method of claim 17, wherein the transducer shaft comprises a transducer shaft of a separate motor and transducer rheometer.

26. The method of claim 17, wherein the motor drive shaft is driven by a motor of a separate motor and transducer rheometer.

27. The method of claim 17, wherein the moveable cylinder is rotated around the axis of the fixed cylinder in substantially the same angular direction that the moveable cylinder is rotated around an axis of the moveable cylinder.

28. The method of claim 17, wherein the moveable cylinder is rotated around the axis of the fixed cylinder in substantially the opposite angular direction that the moveable cylinder is rotated around an axis of the moveable cylinder.

29. The method of claim 17, wherein the moveable cylinder and fixed cylinder are axially separated during the rotation of the moveable cylinder around the axis of the fixed cylinder and the rotation of the moveable cylinder around the axis of the moveable cylinder.

30. The method of claim 29, wherein the portion of the sample not touching the moveable cylinder and the fixed cylinder is not substantially orthogonal to the axis of the moveable cylinder and the axis of the fixed cylinder.

* * * * *